United States Patent

Ho et al.

[11] Patent Number: 5,841,013
[45] Date of Patent: Nov. 24, 1998

[54] AROMATICS HYDROGENATION WITH A NEW CLASS OF METAL OXIDES

[75] Inventors: Teh Chung Ho, Bridgewater; Charles Ralph Symon, Rahway; Viktor Buchholz, Branchburg, all of N.J.; Michel Daage, Baton Rouge, La.

[73] Assignee: Exxon Research and Engineering Company, Florham Park, N.J.

[21] Appl. No.: 857,605

[22] Filed: May 16, 1997

Related U.S. Application Data

[60] Continuation-in-part of Ser. No. 460,318, Jun. 2, 1995, which is a division of Ser. No. 245,180, May 17, 1994, abandoned.

[51] Int. Cl.⁶ .................................. C07C 5/10; B01J 31/00
[52] U.S. Cl. .................... 585/269; 585/266; 502/167; 502/165; 502/200
[58] Field of Search .................... 502/165, 167, 502/219, 162, 159, 200; 585/266, 269, 276, 277

[56] References Cited

U.S. PATENT DOCUMENTS

| | | | |
|---|---|---|---|
| 3,673,112 | 6/1972 | Levinsen | 252/441 |
| 3,755,147 | 8/1973 | Michelson | 208/112 |
| 3,766,058 | 10/1973 | Hensley, Jr. | 208/210 |
| 3,798,156 | 3/1974 | Hensley, Jr. | 208/216 |
| 4,019,976 | 4/1977 | Cosyns et al. | 208/57 |
| 4,021,330 | 5/1977 | Satchell, Jr. | 208/89 |
| 4,595,672 | 6/1986 | Ho et al. | 502/219 |
| 4,622,128 | 11/1986 | Young et al. | 208/18 |
| 4,716,139 | 12/1987 | Jacobson et al. | 502/167 |
| 4,831,002 | 5/1989 | Ho et al. | 502/165 |
| 4,902,404 | 2/1990 | Ho | 208/57 |
| 5,122,258 | 6/1992 | Eadie et al. | 208/112 |
| 5,138,111 | 8/1992 | Kugler et al. | 585/277 |

FOREIGN PATENT DOCUMENTS

| | | | |
|---|---|---|---|
| 1412641 | 11/1975 | United Kingdom | B01J 23/06 |
| 1504951 | 3/1978 | United Kingdom | C10G 23/02 |

*Primary Examiner*—Bekir L. Yildirim
*Attorney, Agent, or Firm*—Linda M. Scuorzo

[57] ABSTRACT

The present invention is directed toward a hydrogenation process using a highly active aromatics hydrogenation catalyst. The catalyst is prepared by decomposing a catalyst precursor selected from the group consisting of metal amine molybdates, metal amine tungstates and mixtures thereof, wherein said metal amine catalyst precursor has the general formula ML $(Mo_yW_{1-y}O_4)_a$ where M is Cr and/or one or more divalent promoter metals selected from the group consisting of Mn, Fe, Co, Ni, Cu and Zn; L is one or more neutral nitrogen-containing ligands at least one of which is a chelating polydentate ligand; $0 \leq y \leq 1$; and a=1 for non-chromium containing catalysts and wherein $0.5 \leq a \leq 3$ for chromium containing catalysts, at a temperature of about 200° C. to about 400° C. in an inert atmosphere; then reducing at a temperature of about 300° C. to about 450° C. said metal amine catalyst precursor to form a mixed metal oxide catalyst of the formula $ML(Mo_yW_{1-y}O_b)_a$ where M, L and y are as above and b<4. The catalyst as prepared above is used in an aromatics hydrogenation processes.

3 Claims, No Drawings

AROMATICS HYDROGENATION WITH A NEW CLASS OF METAL OXIDES

This is a Continuation-In-Part of U.S. Ser. No. 460,318 filed on Jun. 2, 1995 abandoned, which is a Rule 60 Divisional of U.S. Ser. No. 245,180 filed on May 17, 1994 (now abandoned).

FIELD OF THE INVENTION

The present invention is directed to a new class of hydrotreating catalysts and their use in an aromatics hydrogenation process.

BACKGROUND OF THE INVENTION

Aromatics hydrogenation is an integral part of commercial hydro-processing processes which are becoming increasingly important in the face of mounting public concern over the environment and declining crude quality.

The need for highly active aromatics hydrogenation catalysts is particularly pressing because high processing temperatures are thermo-dynamically unfavorable and high pressures require undesirably large capital expenditures. Therefore, tremendous efforts are being expended on the development of new and improved aromatics hydrogenation catalysts.

Conventional metal-based catalysts are active for aromatics hydrogenation, however, they are intolerant of any sulfur compounds and are also very costly. Conventional supported metal sulfide hydrotreating catalysts, which were designed primarily for heteroatom removal, are sulfur tolerant but are far less active than metal-based catalysts.

Hence, there remains a need to find a highly active sulfur tolerant catalyst for aromatics hydrogenation processes.

SUMMARY OF THE INVENTION

The present invention is directed toward a highly active aromatics hydrogenation using a reduced mixed metal oxide catalyst. The catalyst is prepared by:

(a) decomposing a catalyst precursor selected from the group consisting of metal amine molybdates, metal amine tungstates and mixtures thereof, wherein said metal amine catalyst precursor has the general formula

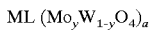
ML $(Mo_yW_{1-y}O_4)_a$ where M is Cr and/or one or more divalent promoter metals selected from the group consisting of Mn, Fe, Co, Ni, Cu and Zn; L is one or more neutral nitrogen-containing ligands at least one of which is a chelating polydentate ligand; $0 \leq y \leq 1$; for non-chromium containing catalysts a=1 and for chromium containing catalysts $0.5 \leq a \leq 3$, at a temperature of about 200° C. to about 400° C. in an inert atmosphere; then (b) reducing at a temperature of about 300° C. to about 450° C. said metal amine catalyst precursor to form a mixed metal oxide catalyst having the general formula

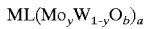
$ML(Mo_yW_{1-y}O_b)_a$ wherein b<4 and M, L and y are as stated for step (a).

The catalyst as prepared above is useful in aromatics hydrogenation processes.

The present invention may comprise, consist or consist essentially of the elements and steps disclosed herein and may be practiced in the absence of a limitation not disclosed.

DETAILED DESCRIPTION OF THE INVENTION

The preparation of the metal amine molybdate or tungstate catalyst precursors used in this work has been detailed in U.S. Pat. Nos. 4,595,672, 4,831,002 and 4,902,404 herein incorporated by reference.

In the present invention aromatics hydrogenation processes are carried out using a reduced mixed metal oxide (i.e., non-sulfided) catalyst. The catalyst can be derived from two types of precursors. In one case, the catalyst is derived from a precursor represented by ML $(Mo_yW_{1-y}O_4)_a$ where M is Cr and/or one or more divalent promoter metals selected from the group consisting of Mn, Fe, Co, Ni, Cu and Zn; L is one or more neutral, nitrogen-containing ligands at least one of which is a chelating polydentate ligand; $0 \leq y \leq 1$; and a–1 when Cr is not one of the metals represented by M, $0.5 \leq a \leq 3$ or more preferably $0.8 \leq a \leq 2$ when Cr is one of the metals represented by M or without another promoter metal.

Preferably, M will be selected from the group consisting of: (a) Ni, Co, Fe and mixtures thereof, and (b) mixtures of (a) with Zn, Cu, Mn, and Cr. Still more preferably, M will be selected from the group consisting of Fe, Mn, Ni, Co, Cr and mixtures thereof. Thus, the promoter metal may be a single metal such as Co, in which case the precursor will have the formula $(CoL)(Mo_yW_{1-y}O_4)$. Alternatively the promoter metal may be a mixture of two, three, four, five, or even six promoter metals. For the case of two promoter metals, such as Ni and Co, the precursor will have the formula $[(Ni_bCo_{1-b})L](Mo_yW_{1-y}O_4)$ where 0<b<1, and so on for the case where 3, 4, 5 or 6 promoter metals are present. The precursor may be a self-promoted molybdate, tungstate or combinations thereof. If it is a molybdate, then y will have a value of 1. Alternatively, if the precursor is tungstate, y will be zero.

The ligand L, will generally have a density of six and will be one or more neutral, nitrogen-containing ligands wherein at least one of said ligands, is a multidentate chelating ligand which chelates the promoter metal to form a chelated promoter metal cation $[ML]^{2+}$. Thus, the catalytic metal oxide anion $(Mo_yW_{1-y}O)^{2-}$ will be ionically bound to the chelated promoter metal cation $[ML]^{2+}$. By neutral is meant that the ligand itself does not have a charge.

Those skilled in the art know that the term "ligand" is used to designate functional coordinating groups which have one or more pairs of electrons available for the formation of coordinate bonds. Ligands that can form more than one bond with a metal ion are called polydentate while ligands that can form only one bond with a metal ion are called monodentate. Monodenitate ligands are not capable of forming chelates. Hence, if one uses one or more species of monodentate ligands in the precursor molecule, then one must also use at least one polydentate chelating ligand. Preferably, L will be one or more polydentate chelating ligands. The denticity of the ligand L will generally be six, because the promoter metal cations prefer six-fold coordination. Hence, if more than one species of ligand is employed in the precursor molecule, the denticity of the ligand species will usually add up to six. It should be understood that it is possible for ligand L to have a total denticity of less than six, but in most cases L will have a total denticity of six. Thus, L will be three bidentate ligands, two tridentate ligands, a mixture of a bidentate and a quadridentate ligand, a hexadentate ligand or a mixture of a polydentate ligand with mono-dentate ligands, as long as the combination has a total denticity of six. As has heretofore been stated, it is preferred to use chelating bidentate and tridentate ligands. In general, the ligands useful in this invention include alkyl and aryl amines and nitrogen heterocycles. Illustrative, but non-limiting examples of ligands useful in the catalyst precursors of this invention are set forth below.

Monodentate ligands will include $NH_3$, as well as alkyl and aryl amines such as ethyl amine, dimethyl amines, pyridine, etc. Useful chelating bidentate amine ligands are illustrated by ethylenediamine, 2,2'-bipyridine, 1,10-phenylene bis(dimethyl-amine), o-phenylene diamine, tetramethylethylenediamine and propane-1,3 diamine. Similarly, useful chelating tridentate amine ligands are represented by terpyridine and diethylenetriamine while triethylerletetramine is illustrative of a useful chelating quadradentate amine ligand. Useful chelating pentadentate ligands include tetraethylenepenetamine while sepulchrate (an octazacryptate) is illustrative of a suitable chelating hexadentate ligand.

However, as a practical matter it will be preferred to use chelating, polydentarte alkyl amines for L. Illustrative, but not limiting examples of alkyl amines that are useful in the catalyst precursor of this invention include ethylenediamine, diethylenetriamine, and tetraethylenetetramine. It is particularly preferred to sue bidentate and tridentate alkyl amines such as ethylenediamine and diethylene-triamine.

In general, the precursor salts useful for forming the reduced mixed metal oxide catalysts and which are represented by the aforementioned formula when M is not Cr, may be prepared by mixing an aqueous solution of ammonium molybdate and/or tungstate with an aqueous solution of chelated promoter metal cation, for example, $[ML]^{2+}$ which, in the presence of excess metallate ligand and/or chelated promoter metal cation, will result in the formation of the precursor salt as a precipitate which is readily recovered. The chelating promoter cation is easily formed by, for example, mixing an aqueous solution of one or more water soluble promoter metal salts with the ligand or mixture of ligands. The water soluble salt may be any water soluble salt that is convenient to use. Non-limiting examples of such salts include halides, sulfates, perchlorates, acetates, nitrates, etc. Alternatively, an aqueous solution of ammonium molybdate and/or tungstate may be mixed with the ligand with the resulting solution mixed with an aqueous solution of promoter metal salt. The salt can also be added to the ligand and dissolved into the solution of molybdate and/or tungstate. It should be understood that the catalyst precursor preparation is not intended to be limited to aqueous media.

When the catalyst contains chromium, two different procedures can be used for the precursor preparation. In the first procedure, the chromium containing precursor is prepared by mixing a slurry of (i) a hydrated oxide of trivalent chromium $Cr(OH)_3 \cdot xH_2O$, with (ii) one or more of the promoter metal and ligand containing metallate salts and, optionally, (iii) one or more metallate salts of Mo and/or W containing the conjugate acid of one or more ligands, but no divalent promoter metal. The metallate salt is then precipitated onto the slurried particles of hydrated chromium oxide and the precursor is recovered. The hydrated chromium oxide may be freshly precipitated from an aqueous solution of a trivalent chromium salt. Alternatively, the source of hydrated chromic oxide may be a colloidal, aqueous suspension of same. In one method of preparation the hydrated chromium oxide will be precipitated from an aqueous solution of trivalent chromium salt by contacting said salt solution with one or more basic amine chelating agents.

In one embodiment, a water soluble trivalent chromium compound and divalent metal salt are dissolved in water and hydrated chromium oxide is precipitated by addition of a ligand, L, or a mixture of ligands, L. This procedure produces a slurry or suspension of very fine particles of a hydrated oxide of trivalent chromium in the aqueous phase, which also contains some free ligand L, and some of the conjugate acid of the ligand L, L'. When the conjugate acid is a strong acid, that is, if the ligand L is a weak base, then a quantity of ammonium hydroxide may be added to precipitate the chromium. The water soluble chromium salt may be any water soluble salt that is convenient to use such as halide, sulfate, nitrate, etc. Sufficient ligand L is added to form the water soluble chelated promoter metal cations $[ML]^{2+}$. This suspension of hydrated chromium oxide containing $[ML]^{2+}$ in solution is then mixed with a solution of the metallate prepared by dissolving ammonium metallate in an excess of the ligand or mixture of ligands. A small amount of water may be added if desired. On mixing the slurry with the metallate solution, an orange-red colored precipitate of the catalyst precursor forms which is recovered by filtration. This precipitate will be a precursor of a composition of this invention. Any step of this preparation may be done in the presence of a slurry of support material. If the chromia is present in sufficient amount, then the excess will serve as all or a portion of the support.

In another embodiment the metallate salts $(ML)(Mo_yW_{1-y}O_4)$ and $(L')(Mo_yW_{1-y}O_4)$ may be prepared separately and mixed separately or together with the hydrated chromium oxide slurry prepared as described above. Again, this may be done in the presence of a slurry of support material. If the chromia is present in sufficient amount, then the excess chromia will comprise all or a portion of the support.

The salts $(L')(Mo_yW_{1-y}O_4)$ may generally be prepared by dissolving the ammonium metallate in excess of the ligand L. The salt is recovered as a precipitate by addition of water or some other suitable antisolvent such as methanol or acetone. If desired, these salts may be formed in the presence of one or more precursor materials as well as in the presence of one or more support materials. This procedure and precursor have more fully been discussed in U.S. Pat. No. 4,622,128 which is incorporated herein by reference.

The second way chromium-containing precursors can be prepared is by mixing a solution of an appropriate metallate such as ammonium molybdeite and/or tungstate in a mixture of ligand(s) L and water with an aqueous solution of the chelated promoter metal cation, containing trivalent chromium $[Cr_{1-z}M_zL_x]^{2n+}$, which results in the formation of the precursor compound as a precipitate which is readily recovered. The chelated, trivalent chromium containing cation is formed under anhydrous conditions by dissolving a soluble salt of trivalent chromium, such as $CrCl_3$, in an appropriate ligand or ligand mixture at low temperature (i.e., 0° C.). When this solution is warmed up to ambient temperature, the chelating reaction occurs and the chelated salt precipitates. The product can be filtered, washed with methanol and dried for subsequent use. The chelated divalent metal promoter cation is easily formed by, for example, mixing an aqueous solution of one or more water soluble promoter metal salts with the ligand. The water soluble salt may be any water soluble salt that is convenient to use such as a halide, sulfate, perchlorate, acetate, nitrate, etc. While the chelated salts are generally water soluble, they can be precipitated from their aqueous solutions by the addition of methanol, filtered and washed with methanol, and dried. For example, solid $Ni(en)_3CL_2$ can be prepared by adding ethylenediamine (en) to an aqueous solution of $NiCl_2 \cdot 6H_2O$, adding methanol to precipitate the chelate, washing with methanol and drying.

The anhydrously prepared chelated chromium cation salt is dissolved in water along with the chelated divalent promoter salt. The ammonium metallate solution is mixed with this solution containing the chelated promoters, resulting in the precipitation of the catalyst precursor. This procedure and precursor are more fully discussed in U.S. Pat. No. 4,831,002 which is incorporated herein by reference.

The difference in the method of preparing the chelated chromium promoter cation from the chelated divalent metal promoter cations is the fact that chromium chelation is slow compared to that of the divalent ions. As a result, the addition of the basic ligand to an aqueous chromium salt solution will result in the formation predominantly of hydrated chromium oxide instead of the chelate $(CrL)Cl_3$. To avoid this hydrated oxide formation, the chromium chelation is carried out under anhydrous conditions by adding the trivalent chromium salt to the dry ligand. One can prepare the divalent promoter metal chelates in the same manner, either separately or along with the trivalent chromium chelates.

The resulting mixed metal oxide catalysts are represented by the formula $ML(Mo_yW_{1-y}O_b)_a$ where M is Cr and/or one or more divalent promoter metals selected from the group consisting of Mn, Fe, Co, Ni, Cu and Zn; L is one or more neutral nitrogen-containing ligands at least one of which is a chelating polydentate ligand; $0 \leq y \leq 1$; for non-chromium containing catalysts a=1; for chromium containing catalysts $0.5 \leq a \leq 3$; and b is <4.

The resulting mixed metal oxide catalysts may be used in bulk or supported on a suitable support, preferably supported on a suitable inorganic refractory oxide support such as alumina. The catalysts can be supported by techniques known to those skilled in the art, such as, impregnation, incipient wetness, and the like, with the choice being left to the individual practitioner.

The reduced mixed metal oxides catalysts are used for aromatics hydrogenation reactions. The principal operating variables are temperature, hydrogen partial pressure, treat gas rate and space velocity. Typical ranges of process variables are 300°–800° F., 100–3,000 psig pressure (689.5 to 20,684.3 kPa) hydrogen, 300–3,000 scf/bbl; LHSV 0.5–8.0.

In another aspect of the invention, the instant catalysts are utilized in a stacked bed system. The instant cobalt molybdenum catalysts are placed downstream of the instant nickel molybdenum catalysts. Such a system provides an activity synergism. The catalysts in such a configuration interact in a nonlinear manner yielding a greater activity than the sum of the activities of each catalyst. In the stacked bed system, the catalyst with the higher activity is placed downstream. Activities are readily determinable by one skilled in the art.

The invention will be further understood by reference to the following nonlimiting examples.

The following activity tests were conducted in an automated fixed bed unit consisting of two independent upflow reactors in a common sand bath. Each reactor was equipped with a calibrated feed burette, a pump, a gas-liquid separator, and a product liquid collector. The reactor was made of a ⅜-inch ID) 316 stainless steel pipe. The reactor pressure, temperature and hydrogen flow rate were all controlled by a computer. The catalyst particles were crushed and sized to 20–40 mesh granules to ensure adequate particle to reactor diameter ratios in the activity tests. Each reactor was packed with 10 cc of catalyst in the central zone and inert materials in the fore and aft zones. The attainment of isothermal conditions was indicated by temperature measurement across the bed with four equally spaced thermalcouples.

The feed contains 7.2 wt % 2-methylnaphthalene, with the balance being hexadecane. The reaction conditions were 3.15 MPa, 1.0 LHSV, 1000 SCF/BBL, and 240°–260° C. The liquid products were quantified on a Hewlett Packard (HP) gas chromatograph. The hydrogenation proceeds as follows:

$$m\text{-}N \rightarrow m\text{-}T \rightarrow m\text{-}D$$

where m-N, m-T and m-D denotes methylnaphthalene, methyltetralines, and methyldecalines, respectively.

Prior to use, the precursor compounds were thermally decomposed to remove the organic constituents in flowing $N_2$. This is followed by reduction in hydrogen at elevated temperatures (300°–450° C.).

EXAMPLE 1

This example shows the criticality of preactivating the catalysts with $H_2$ at an elevated temperature. The comparative experiments were done with bulk NiMo oxide prepared from nickel tris (ethylenediamine) molybdate. In one experiment, the catalyst was charged to the reactor immediately after the thermal decomposition in nitrogen and run with the methylnaphthalene feed at 240° C. In another experiment, the catalyst was $H_2$-treated in situ at 375° C. for 3 hours before being put on stream. The raw data are summarized in Table 1.

TABLE 1

Effect of In Situ $H_2$ Treatment: Bulk NiMo Oxide

| Catalyst | Temperature, °C. | Composition of Reaction Products, wt % | | |
| --- | --- | --- | --- | --- |
| | | m-N | m-T | m-D |
| without $H_2$ treatment | 240 | 7.0 | 0.25 | 0.0 |
| with $H_2$ treatment | 240 | 2.0 | 4.6 | 0.42 |
| with $H_2$ treatment | 260 | 0.2 | 6.0 | 1.0 |

As can be seen, reduction with $H_2$ resulted in a substantial increase in activity. At 260° C., although the conversion of methylnaphthalene is nearly complete, the primary reaction product is m-tetralins.

EXAMPLE 2

Here we show the criticality of metal composition. The following catalyst compositions, all of which were prepared from metal amine molybdates which were reduced with $H_2$, were evaluated: NiMo, CoMo, and $Ni_{.5}Mn_{.5}Mo$. As Table 2 shows, the CoMo catalyst exhibits by far the highest activity. It produced a significantly higher amount of methyldecalins than the other two catalysts even at a lower temperature.

TABLE 2

Effect of Metal Composition

| Catalyst Metal Compositions | Temperature, °C. | Composition of Reaction Products, wt % | | |
| --- | --- | --- | --- | --- |
| | | m-N | m-T | m-D |
| $Ni_{.5}Mn_{.5}Mo$ | 260 | 0.0 | 6.8 | 0.4 |
| NiMo | 260 | 0.2 | 6.0 | 1.0 |
| CoMo | 240 | 0.0 | 2.3 | 5.1 |

EXAMPLE 3

This example demonstrates that a stacked bed—with a particular stacking order—can give rise to an activity synergism. Two experimental runs were made. In one case, the CoMo catalyst was placed upstream of the NiMo catalyst (stacked bed A). In another case, the stacking order was reversed (stacked bed B). In both runs, each of the constituent catalysts in the stacked bed occupies 50% of the bed volume. The results are summarized in Table 3.

TABLE 3

Hydrogenation in Stacked Bed

| Catalyst | Temperature, °C. | Composition of Reaction Products, wt % | | |
|---|---|---|---|---|
| | | m-N | m-T | m-D |
| A | 240 | 0.0 | 6.3 | 1.0 |
| | 260 | 0.0 | 5.8 | 1.4 |
| B | 240 | 0.0 | 4.0 | 3.3 |
| | 260 | 0.0 | 3.2 | 4.2 |

Evidently, the stacking order has a strong effect on the overall performance of the stacked bed, indicating that the two constituent catalysts interact with each other in a nonlinear manner. The preferred configuration is to put NiMo (the less active catalyst) upstream of CoMo (the more active catalyst). With this configuration, the overall activity is greater than would be predicted from a weighted sum of the activities of the constituent catalysts.

What is claimed is:

1. A catalyst composition of the formula $ML(Mo_yW_{1-y}O_b)_a$ wherein M is Cr and/or one or more divalent promoter metals selected from the group consisting of Mn, Fe, Co, Ni, Cu and Zn, L is one or more neutral nitrogen containing ligands at least one of which is a chelating polydentate ligand, $0 \leq y \leq 1$, for non-chromium containing catalysts a=1, for chromium containing catalysts $0.5 \leq a \leq 3$, and b<4.

2. An aromatics hydrogenation process, comprising: contacting a mixed metal oxide catalyst having the formula $$ML(Mo_yW_{1-y}O_b)_a$$

wherein M is Cr and/or one or more divalent promoter metals selected from the group consisting of Mn, Fe, Co, Ni, Cu and Zn, L is one or more neutral nitrogen-containing ligands at least one of which is a chelating polydentate ligand, $0 \leq y \leq 1$, and a=1 for non-chromium containing catalysts and wherein $0.5 \leq a \leq 3$ for chromium containing catalysts, and b is <4, prepared by process of (a) decomposing a catalyst precursor selected from the group consisting of metal amine molybdates, metal amine tungstates and mixtures thereof, wherein said metal amine catalyst precursor has the general formula $$ML(Mo_yW_{1-y}O_4)_a$$

wherein M is Cr and/or one or more divalent promoter metals selected from the group consisting of Mn, Fe, Co, Ni, Cu and Zn, L is one or more neutral nitrogen-containing ligands at least one of which is a chelating polydentate ligand, $0 \leq y \leq 1$, for non-chromium containing catalysts a=1, for chromium containing catalysts $0.5 \leq a \leq 3$, at a temperature of about 200° C. to about 400° C. in an inert atmosphere; then (b)) reducing at a temperature of about 300° C. to about 450° C. said metal amine catalyst precursor to form said mixed metal oxide catalyst with a hydrocarbon feedstream under aromatics hydrogenation process conditions.

3. An aromatics hydrogenation process, comprising: contacting a hydrocarbon feedstream under aromatics hydrogenation conditions with a stacked bed catalyst system comprising a first and a second mixed metal oxide catalyst having the formula $$ML(Mo_yW_{1-y}O_b)_a$$

wherein M is Cr and/or one or more divalent promoter metals selected from the group consisting of Mn Fe, Co, Ni, Cu and Zn, L is one or more neutral nitrogen-containing ligands at least one of which is a chelating polydentate ligand, $0 \leq y \leq 1$, and a=1 for non-chromium containing catalysts and wherein $0.5 \leq a \leq 3$ for chromium containing catalysts, and b is <4, wherein said first and said second mixed metal oxide catalysts are prepared by the process of:

(a) decomposing a catalyst precursor selected from the group consisting of metal amine molybdates, metal amine tungstates and mixtures thereof, wherein said metal amine catalyst precursor has the general formula $$ML(Mo_yW_{1-y}O_4)_a$$

where M is Cr and/or one or more divalent promoter metals selected from the group consisting of Mn, Fe, Co, Ni, Cu and Zn; L is one or more neutral nitrogen-containing ligands at least one of which is a chelating polydentate ligand; $0 \leq y \leq 1$; and a=1 for non-chromium containing catalysts and wherein $0.5 \leq a \leq 3$ for chromium containing catalysts, at a temperature of about 200° C. to about 400° C. in an inert atmosphere; then (b) reducing at a temperature of about 300° C. to about 450° C. said metal amine catalyst precursor to form said mixed metal oxide catalyst and wherein the catalyst having the greater activity is the second catalyst.

* * * * *